(12) United States Patent
Benz et al.

(10) Patent No.: US 9,561,302 B2
(45) Date of Patent: Feb. 7, 2017

(54) ULTRAVIOLET LIGHT ABSORBING MATERIALS FOR INTRAOCULAR LENS AND USES THEREOF

(75) Inventors: Patrick H. Benz, Sarasota, FL (US); Adam Reboul, Sarasota, FL (US)

(73) Assignee: Benz Research & Development Corp., Sarasota, FL (US)

( * ) Notice: Subject to any disclaimer, the term of this patent is extended or adjusted under 35 U.S.C. 154(b) by 0 days.

(21) Appl. No.: 13/619,043

(22) Filed: Sep. 14, 2012

(65) Prior Publication Data

US 2013/0096273 A1  Apr. 18, 2013

Related U.S. Application Data

(60) Provisional application No. 61/535,849, filed on Sep. 16, 2011, provisional application No. 61/599,756, filed on Feb. 16, 2012.

(51) Int. Cl.

| A61F 2/16 | (2006.01) |
|---|---|
| A61L 27/00 | (2006.01) |
| C08F 126/06 | (2006.01) |
| C08F 220/28 | (2006.01) |
| C08F 220/36 | (2006.01) |
| G02B 1/04 | (2006.01) |

(52) U.S. Cl.
CPC .............. *A61L 27/00* (2013.01); *A61F 2/16* (2013.01); *A61F 2/1613* (2013.01); *A61F 2/1659* (2013.01); *C08F 126/06* (2013.01); *C08F 220/28* (2013.01); *C08F 220/36* (2013.01); *G02B 1/043* (2013.01); *A61F 2002/16905* (2015.04); *A61F 2002/16965* (2015.04)

(58) Field of Classification Search
CPC ....... C08F 126/06; C08F 220/36; A61L 27/16; A61F 2/16; A61F 2/1613; A61F 2/1659; A61F 2002/1905; A61F 2002/16965
USPC ........................................................ 526/261
See application file for complete search history.

(56) References Cited

U.S. PATENT DOCUMENTS

| 5,133,745 | A * | 7/1992 | Falcetta et al. ............. 623/6.61 |
| 6,267,784 | B1 * | 7/2001 | Benz et al. .................. 623/6.59 |
| 6,326,448 | B1 * | 12/2001 | Ojio et al. ................... 526/259 |
| 6,517,750 | B2 | 2/2003 | Benz et al. |
| 7,067,602 | B2 | 6/2006 | Benz et al. |
| 7,387,642 | B2 | 6/2008 | Benz et al. |
| 7,947,796 | B2 | 5/2011 | Benz et al. |
| 2002/0027302 | A1 | 3/2002 | Benz et al. |
| 2002/0058723 | A1 | 5/2002 | Benz et al. |
| 2002/0058724 | A1 | 5/2002 | Benz et al. |
| 2005/0131183 | A1 | 6/2005 | Benz et al. |
| 2006/0199929 | A1 | 9/2006 | Benz et al. |
| 2006/0276606 | A1 | 12/2006 | Benz et al. |
| 2008/0221235 | A1 | 9/2008 | Benz et al. |
| 2010/0113641 | A1 | 5/2010 | Laredo |
| 2010/0324165 | A1 | 12/2010 | Ritter et al. |

FOREIGN PATENT DOCUMENTS

| EP | 2465880 A1 | 6/2012 |
| JP | 09028785 A * | 2/1997 |
| JP | 9-028785 | 4/1997 |
| JP | 2005-508423 A | 3/2005 |
| JP | 2005-531365 A | 10/2005 |
| JP | 2011-505932 A | 3/2011 |
| WO | WO 2011/018990 A1 | 2/2011 |
| WO | WO2011/069931 A1 | 6/2011 |

OTHER PUBLICATIONS

International Search Report and Written Opinion for Application No. PCT/US2012/055561, mail date Dec. 17, 2012, 9 pages.
U.S. Appl. No. 61/535,795, filed Sep. 16, 2011, Benz et al.
Office Action mailed Oct. 5, 2015 in related European Appl. No. 12775349.9 (6 pgs.).
Office Action mailed Jun. 28, 2016 in related Japanese appl. 2014-530891 with English-language translation (9 pgs.).

* cited by examiner

*Primary Examiner* — Ling Choi
*Assistant Examiner* — David L Miller
(74) *Attorney, Agent, or Firm* — Foley & Lardner LLP

(57) ABSTRACT

A method for reducing the transmittance of ultraviolet radiation through an intraocular lens to 10% or less at 370 mm Additionally, a method for preventing the transmittance of at least 90% of ultraviolet radiation at 370 nm through a foldable intraocular lens comprising: (a) incorporating a monomer comprising a 4-(4,6-diphenyl-1,3,5-triazin-2-yl)-3-hydroxyphenoxy moiety into at least one polymer and (b) forming the polymer into a material suitable for use as an intraocular lens, wherein the monomer comprising a 4-(4, 6-diphenyl-1,3,5-triazin-2-yl)-3-hydroxyphenoxy moiety comprises 0.10 to 0.15 weight percent of the overall dry polymer.

45 Claims, 1 Drawing Sheet

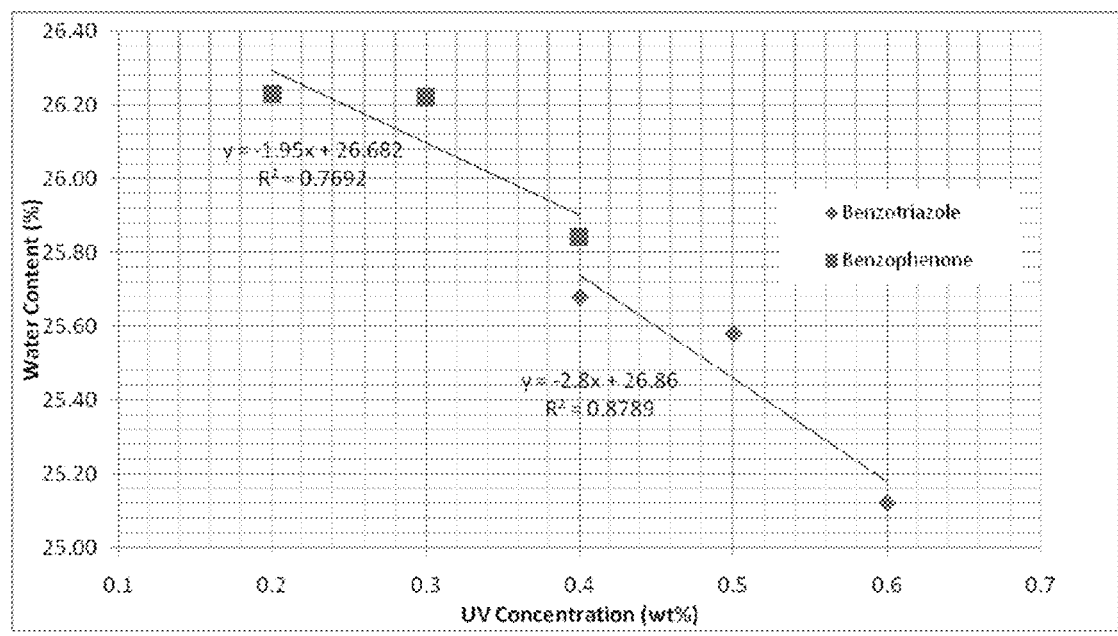

ULTRAVIOLET LIGHT ABSORBING MATERIALS FOR INTRAOCULAR LENS AND USES THEREOF

RELATED APPLICATIONS

This application claims priority to U.S. provisional application Ser. No. 61/535,849 filed Sep. 16, 2011 and U.S. provisional application Ser. No. 61/599,756 filed Feb. 16, 2012, the complete disclosure of each is hereby incorporated by reference in its entirety.

BACKGROUND

Various polymeric compositions used in the formation of intraocular lenses (IOLs) are known. Formation of these polymeric compositions from various monomers of different functionality can dramatically affect the properties of the resulting IOL. Often a monomer capable of absorbing ultraviolet (UV) radiation is incorporated into the polymeric composition. Addition of the UV-absorbing monomer can change the overall composition of the polymer, and thus can dramatically affect the properties of the resulting IOL. For examples of IOL materials and methods of making, see, e.g., U.S. Pat. Nos. 7,947,796, 7,387,642, 7,067,602, 6,517,750 and 6,267,784 each of which is hereby incorporated by reference in its entirety. Additionally, see U.S. Patent Publication Nos. 2008/0221235, 2006/0276606, 2006/0199929, 2005/0131183, 2002/0058724, 2002/0058723 and 2002/0027302 each of which is hereby incorporated by reference in its entirety.

Many UV absorbing compounds contain aromatic pi-electron systems that are known to change characteristics of a final polymer, such as for example refractive index. Furthermore, increasing the concentration of UV-absorbing monomer may change the overall hydrophilicity or hydrophobicity of the polymer due to the presence of additional UV-absorbing moieties in the polymer. Therefore, addition of a substantial amount of a new component to an IOL polymer composition, may result in significant change to the properties of the compound, which already may have established commercial and/or regulatory significance to an already existing product.

Already existing IOL products that contain UV-absorbing moieties within the polymeric compound, such as for example those comprising a benzophenone moiety, may not provide adequate UV absorbing at certain wavelengths without a substantial increase in the concentration of the benzophenone moiety from currently developed compositions. The substantial increase in UV absorbing moiety, such as benzophenone, may alter the physical properties of the resulting compound and thereby require reformulation and/or recertification of a commercial compound. Therefore, a need exists for the incorporation of UV-absorbing compounds that can be incorporated into a polymeric composition suitable for IOLs in concentrations low enough as to not significantly alter the characteristics of the IOL—other than transmittance of UV—when compared to the same formulation without the new UV-absorbing compound. The new compound, for these needs, should impart UV-absorbing properties so that the formed IOL may reduce transmittance of UV rays by at least 90% at a wavelength of 370 nm.

SUMMARY

Embodiments described herein include, for example, methods of making and using copolymers, lenses, intraocular lenses, blanks for intraocular lenses comprising a trisaryl-1,3,5-triazine moiety to reduce transmission of radiation without substantially affecting other characteristics of the copolymers, lenses, intraocular lenses and blanks for intraocular lenses.

One embodiment provides, for example, method of making an intraocular lens capable of reducing the transmittance of ultraviolet radiation at 370 nm comprising: (a) polymerizing a mixture comprising: at least one first monomer and at least one second monomer comprising a trisaryl-1,3,5-triazine moiety, and (b) forming an optic portion from the copolymer wherein the second monomer is present in an amount sufficient to reduce the transmittance of ultraviolet radiation at 370 nm to ten percent or less, and wherein the amount of the second monomer does not substantially affect a physical characteristic of the lens other than transmittance of ultraviolet radiation.

Another embodiment, provides, for example, a method of making an intraocular lens capable of absorbing ultraviolet radiation at 370 nm comprising: (a) polymerizing a mixture comprising: at least one first monomer and at least one second monomer comprising a trisaryl-1,3,5-triazine moiety, and (b) forming an optic portion from the copolymer wherein the second monomer is present in about 0.10 to about 0.20 percent by weight of the overall dry polymer and wherein the optic portion of the intraocular lens displays essentially the same refractive index as the optic portion of the intraocular lens formed from the polymerized mixture of (a) without the second monomer, but otherwise identical conditions.

Another embodiment, provides, for example, a method for preventing the transmittance of at least 90% of ultraviolet radiation at 370 nm through a foldable intraocular lens comprising, consisting essentially of, or consisting of: (a) incorporating at least one monomer comprising a 4-(4,6-diphenyl-1,3,5-triazin-2-yl)-3-hydroxyphenoxy moiety into at least one polymer and (b) forming the polymer into a material suitable for use as an intraocular lens, wherein the monomer comprising a 4-(4,6-diphenyl-1,3,5-triazin-2-yl)-3-hydroxyphenoxy moiety comprises 0.10 to 0.20 weight percent of the overall dry polymer.

Another embodiment, provides, for example, a foldable intraocular lens or lens blank comprising at least one copolymer comprising at least (a) one first monomer, and (b) one second monomer present in about 0.05 to about 0.20 percent by weight of the overall dry polymer comprising a 4-(4,6-diphenyl-1,3,5-triazin-2-yl)-3-hydroxyphenoxy moiety, wherein the foldable intraocular lens or lens blank absorbs the transmittance of at least 90% of ultraviolet radiation at 370 nm, and wherein the optic portion of the intraocular lens displays essentially the same refractive index as the optic portion of a intraocular lens formed from the polymerized mixture of (a) without the second monomer, but otherwise identical composition.

At least one advantage for at least one embodiment includes reducing the transmittance of ultraviolet radiation at 370 nm to 10% or less in an intraocular lens, without substantially changing the refractive index of the lens.

At least one advantage for at least one embodiment includes reducing the transmittance of ultraviolet radiation at 370 nm to 10% or less in an intraocular lens, without substantially changing the water content of the lens.

At least one advantage for at least one embodiment includes reducing the transmittance of ultraviolet radiation at 370 nm to 10% or less in an intraocular lens, without substantially changing the glass transition temperature of the lens.

At least one advantage for at least one embodiment includes increasing the aqueous solubility of an embodied composition by providing a substituted alkyl linker in a second monomer, as described herein.

BRIEF DESCRIPTION OF THE FIGURES

FIG. 1 is a graph demonstrating the UV Absorber Impact to Water Content. In the embodiments, the benzotriazole can cause a 2.8% water loss for every 1.0% added to an IOL formulation. Moving the concentration from 0.2% to 0.6% can shift the water content down approx 1.1%.

DETAILED DESCRIPTION

Introduction

All references cited herein are incorporated by reference in their entirety. For the purposes of this application UV absorbing material refers to material that reduces the transmission of UV radiation through said material. Unless indicated otherwise, all component amounts are presented on a % (w/w) basis ("wt. %"). As used herein substantially affecting a physical characteristic or substantially changing a physical characteristic or displaying essentially the same characteristics refer to not changing the physical properties of the polymeric compound, or not changing the physical properties of the compound by more than 1.0%, or not changing the physical properties of the compound by more than 2.0%, or for refractive index measurements, not changing the refractive index by more than 0.1% or not changing the refractive index by more than 0.05%, or for glass transition temperature, not changing the temperature by more than 1° C.

Commercial embodiments of intraocular lens materials generally include a UV-blocking and/or UV-absorbing compound incorporated therein. Many factors can affect the level of transmittance of UV radiation through an IOL. For example, the UV-absorbing compound chosen and/or the concentration of the UV-absorbing compound may alter the percent transmittance of various wavelengths of UV radiation. Additionally, the thickness of the IOL may affect the percent transmission.

Intraocular Lens First Compounds

First compounds of the embodiments contained herein are generally monomers that can be reacted in various concentrations or under various conditions to form a polymeric composition suitable for use as a foldable IOL material. Many compositions or compounds embodied herein are described in the prior art, such as for example, U.S. Pat. Nos. 7,947,796, 7,387,642, 7,067,602, 6,517,750 and 6,267,784 each of which is hereby incorporated by reference in its entirety. Additionally, in U.S. Patent Publication Nos. 2008/0221235, 2006/0276606, 2006/0199929, 2005/0131183, 2002/0058724, 2002/0058723 and 2002/0027302 each of which is hereby incorporated by reference in its entirety. The compositions or compounds of U.S. Provisional 61/535,795, titled Hydrophobic Intraocular Lens, and submitted on September 16, 2011 is hereby incorporated by reference in its entirety. It is generally known in the art that monomers may be used for IOL formation, and disclosure herein of first monomers is not meant to be limiting, but merely to provide exemplary compounds. In an embodiment, the first compound may be at least one compound comprising an acrylate, methacrylate, acrylamide and/or methacrylamide moiety and at least one additional moiety. In some embodiments, the first compound is a hydrophobic molecule containing an acrylate, methacrylate, acrylamide and/or methacrylamide moiety. In other embodiments, the first compound is a hydrophilic molecule containing an acrylate, methacrylate, acrylamide and/or methacrylamide moiety. In some embodiments multiple first compounds containing different functional moieties are polymerized. Embodiments may comprise other compounds suitable for IOL lenses containing at least one polymerizable moiety, such as for example acrylate, acrylamide, methacrylamide and/or methacrylate. For example, some embodiments include at least one hydrophilic molecule containing an acrylate, methacrylate, acrylamide and/or methacrylamide moiety and at least one hydrophobic molecule containing a polymerizable moiety such as for example an acrylate, methacrylate, acrylamide and/or methacrylamide moiety. Other embodiments contain two, three, four or more different hydrophilic and/or hydrophobic molecules containing a polymerizable moiety such as for example an acrylate, methacrylate, acrylamide and/or methacrylamide moiety. Other embodiments contain molecules that may be considered neither hydrophobic nor hydrophilic containing a polymerizable moiety such as for example an acrylate, methacrylate, acrylamide and/or methacrylamide. Some embodiments have an alkacrylate or alkacrylamide moiety wherein the alkyl group is a C2-C5 alkyl group. One skilled in the art would recognize that alkacrylate and alkacrylamide contain the alkyl group covalently bonded to the carbon adjacent to the carbonyl moiety of the alkacrylate or alkacrylamide. Other embodiments contain crosslinkers and/or other compounds such as for example water, a colorant, and/or an antioxidant. In an embodiment the acrylate (A), acrylamide (AA), methacrylamide (MAA) and/or methacrylate (MA) moiety is covalently bound through the O or N atom of the moiety to an additional moiety known in the art to provide monomers suitable for polymerization into foldable IOL compositions. Exemplary, non-limiting monomers include but are not limited in any way to: 2-hydroxy-3-phenoxypropyl-A, hydroxy-3-phenoxypropyl-AA, hydroxy-3-phenoxypropyl-MA, hydroxy-3-phenoxypropyl-MAA, 2-ethoxyethyl-A, 2-ethoxyethyl-MA, 2-ethoxyethyl-AA, 2-ethoxyethyl-MAA, 2-hydroxyethyl-A, 2-hydroxyethyl-AA, 2-hydroxyethyl-MA, 2-hydroxyethyl-MAA, polyethylene glycol monomethyl ether-A, polyethylene glycol monomethyl ether-MA, polyethylene glycol monomethyl ether-AA, polyethylene glycol monomethyl ether-MAA, 2-hydroxy-3-phenoxypropyl-A, 2-hydroxy-3-phenoxypropyl-AA, 2-hydroxy-3-phenoxypropyl-MA, 2-hydroxy-3-phenoxypropyl-MAA, 2-ethoxyethyl-A, 2-ethoxyethyl-AA, 2-ethoxyethyl-MA, 2-ethoxyethyl-MAA, lauryl-A, lauryl-MA, lauryl-AA, lauryl-MAA, glycerol-A, glycerol-MA, glycerol-MAA, glycerol-AA, and additional monomers found within the references incorporated herein. Furthermore, other monomers known by those skilled in the art as capable of forming foldable IOLs may be used with the embodiments herein.

UV Absorbing Compounds

UV-absorbing compounds of the current embodiments comprise compounds containing a trisaryl-1,3,5-triazine moiety wherein at least one of the aryl rings has a hydroxyl group ortho to the point of attachment to the triazine ring. Generally this hydroxyl can be referred to as a latent hydroxy group. In general, this class of materials is known in the art. See U.S. Pat. No. 6,365,652 and references therein. Each of which is hereby incorporated by reference. Compounds containing this moiety have been incorporated into polymers for the purpose of stabilizing a material against the effects of actinic radiation and for the reduction of transmittance of UV radiation through certain polymers. See U.S. Pat. No. 6,365,652 and JP 1997/028785. Compounds embodied herein generally include an additional moiety appended to the trisaryl-1,3,5-triazine compound that is reactive and capable of being incorporated into a polymer during polymerization of other first monomers. In one embodiment, an ether linkage from the trisaryl-1,3,5-triazine to an alkyl linker that is covalently appended to at least one polymerizable moiety, such as for example acrylate, acrylamide, methacrylamide and/or methacrylate. In other embodiments, at least one polymerizable moiety, such as for example acrylate (A), acrylamide (AA), methacrylamide (MAA) and/or methacrylate (MA) moiety can be replaced by another moiety capable of polymerization. The scope of this disclosure is not limited, however, to A, AA, MAA, and MA. Rather, other embodiments, for example, include further substitution of acrylate and acrylamide, such as for example, ethacrylate or ethacrylamide and other polymerizable moieties comprising acrylate and acrylamide functionality. In some embodiments, the ether linkage can be meta to the triazine. In other embodiments the ether linkage can be para to the triazine ring. In other embodiments, the linker can comprise sulfur instead of oxygen.

As used herein the "alkyl linker" may be optionally substituted by one, two, three or four hydroxy, halogen, amine, trifluromethyl, ($C_1$ to $C_5$) alkoxy, ($C_1$ to $C_5$) straight or branched alkyl optionally substituted by one, two, three or four hydroxy, halogen, amine, ($C_1$ to $C_5$) alkoxy or trifluromethyl. For example, in one embodiment, the alkyl linker is substituted by one, two, three or four hydroxyl moieties.

In some embodiments, the UV absorbing compound comprises a compound of the formula (I).

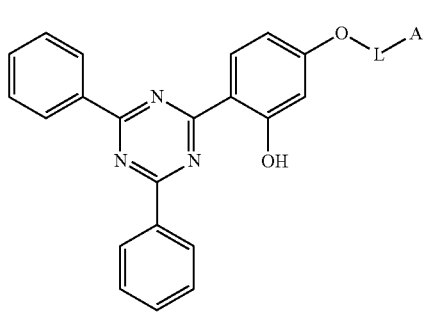

(I)

wherein L is an alkyl linker and A is an acrylate, methacrylate, acrylamide or methacrylamide. In some embodiment L can be selected from alkyl groups having 1 to 5 carbon atoms and in some embodiments 1, 2, 3, 4, or 5 carbon atoms. Alkyl groups that may be used in accordance with the embodiments herein include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —CH(CH$_3$)$_2$, —CH(CH$_3$)(CH$_2$CH$_3$), —CH(CH$_2$CH$_3$)$_2$, —C(CH$_3$)$_3$, and the like. The alkyl linker can also be substituted by one or more polar moieties. The polar moieties include, for example, hydroxy, halogen, amine, trifluromethyl, ($C_1$ to $C_5$) alkoxy, ($C_1$ to $C_5$) straight or branched alkyl optionally substituted by one, two, three or four hydroxy, halogen, amine, ($C_1$ to $C_5$) alkoxy or trifluromethyl. With respect to L, it will be understood that the alkyl linker is bonded to the O of the trisaryl-1,3,5-triazine-O group and is bonded to the O or N atom of the A group. In some embodiments, compounds represented by Formula I L is a $C_1$ to $C_5$ alkyl substituted by one, two, three or four hydroxyl moieties and A is an acrylate or methacrylate, or L is a $C_1$ to $C_5$ alkyl substituted by one hydroxyl moiety and A is an acrylate or methacrylate, or L is represented by the formula —CH$_2$CH(OH)CH$_2$— and A is an acrylate or methacrylate.

In preferred embodiments the UV absorbing monomer can be a compound of the formula (II).

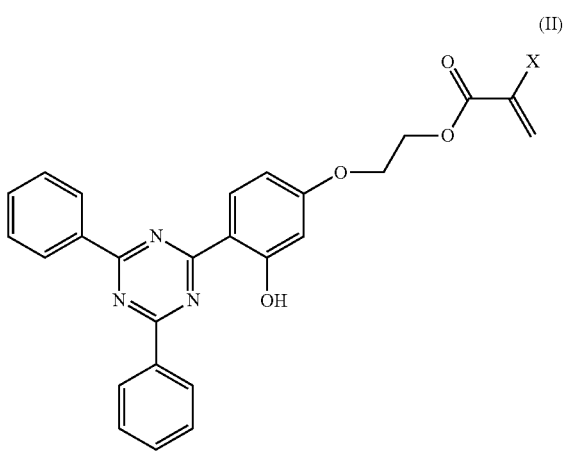

(II)

wherein X is H or CH$_3$.

In another preferred embodiment, the UV absorbing monomer can be a compound of the formula (III).

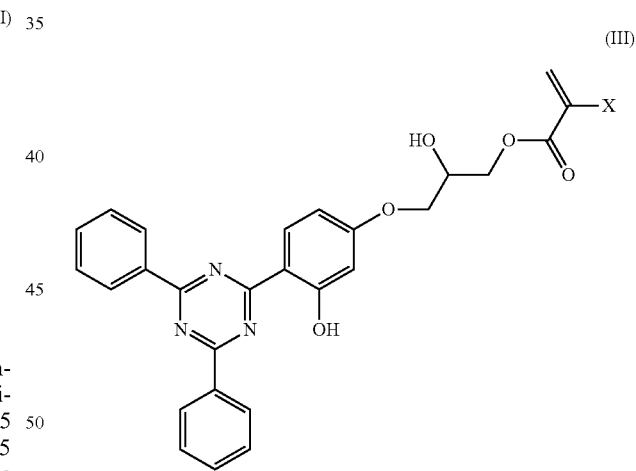

(III)

wherein X is H or CH$_3$.

Amount of UV Absorbing Compounds

In general, some of the UV absorbing compounds embodied herein are a class of materials known in the art. However, the compounds embodied herein are but only one subset of a vast array of compounds known in the art as UV absorbing compounds. In fact, many other compounds, such as for example, those containing benzophenone moiety are known to absorb UV radiation. In many instances, compounds embodied in the present embodiments herein have been previously formulated to meet certain physical characteristics when formed into an IOL. These characteristics are vital to the functionality of the lens and include by way of non-limiting example, refractive index, water content and/or glass transition temperature. Often many of these compositions include a UV absorbing compound, but to meet different UV-blocking or UV-absorbing standards, whether mandated by regulation or consumer need, these previously formed compounds may require additional UV absorbing monomer or compound to achieve desired UV transmittance properties. Often addition of additional UV absorbing compound will lead to a change in IOL characteristics and potentially lead to the need to reformulate the IOL composition. Therefore, a compound capable of blocking or absorbing UV radiation while present in small concentrations is needed.

The UV absorbing monomers of the present embodiments herein are used in a low percentage of the overall dry monomer used to form a polymer suitable for IOL. In some embodiments, the UV absorbing monomer is 0.001 to 0.30 percent by weight of the overall dry monomer used to form a polymer suitable for IOL. In other embodiments, the UV absorbing monomer is 0.05 to 0.20 percent by weight of the overall dry monomer used to form a polymer suitable for IOL. In a more preferred embodiment, the UV absorbing monomer is 0.10 to 0.15 percent by weight of the overall dry monomer used to form a polymer suitable for IOL. It is understood that these ranges are non limiting, and a preferred embodiment may be, for example 0.08 to 0.18 percent by weight or any other suitable range within 0.05 to 0.25 percent by weight of the overall dry monomer used to form a polymer suitable for IOL. In a preferred embodiment the UV absorbing monomer is present from about 0.13 percent to 0.17 percent by weight of the overall dry monomer used to form a polymer suitable for IOL.

In some embodiments, the UV absorbing monomer will be present in an amount sufficient to impart a 5, 6, 7, 8, 9, or 10 percent transmittance of UV radiation of a wavelength of 368, 369, 370, 371, and/or 372 nm in a formed IOL. In a preferred embodiment, the UV absorbing monomer will be present in an amount sufficient to impart a 5, 6, 7, 8, 9, or 10 percent transmittance of UV radiation of 370 nm in a formed IOL. This 5, 6, 7, 8, 9, or 10 percent transmittance of UV radiation of 370 nm may be in an IOL of thicknesses known in the art, such as for example 300 microns to 1000 microns. In other embodiments the UV absorbing monomer will be present in an amount sufficient to impart a 5, 6, 7, 8, 9, or 10 percent transmittance of UV radiation of 370 nm in a foldable, spherical IOL with a diopter from 0 to 35 or 10 to 30 m$^{-1}$. In another embodiment, the IOL or IOL blank contains a UV absorbing monomer with an molar extinction coefficient at 370 nm greater than 3000 M$^{-1}$cm$^{-1}$.

Formation of the Polymer Compositions

As used herein, the term "polymer" refers to a composition that is formed by polymerizing one monomer or two more (different) monomers. The term "polymer" thus includes "homopolymers" formed from only one type of monomer, "copolymers" which are formed from two or more different monomers, "terpolymers" formed from at least three different monomers, and any polymer that is formed from at least one type of monomer and may be formed from one, two, three, four, or more different monomers. The polymers can also be formed from oligomers comprising the oligomerized monomers embodied herein.

In the present polymers, the total quantity of the one or more of the first monomer can make up the majority of the polymer, as measured by weight. The second monomer comprising a trisaryl-1,3,5-triazine moiety can be present as 0.20 wt. % or less of the overall polymers.

The polymers of the embodiments herein can be prepared using conventional polymerization techniques known to those in the field of polymer chemistry. Additionally, the formulation of polymers suitable for IOLs is described in detail in the referenced cited and incorporated herein. Generally, the first polymers and the UV absorbing monomer will polymerized under conditions disclosed herein and in the references incorporated by reference. Crosslinkers, also referred to as crosslinking agents, may be employed in the polymerization reaction. For example, any suitable crosslinking di-functional, multi-functional monomer, or combination of these can be used in effective amounts to give the desired crosslinking density. For example, in a concentration range of 0.4 to about 4 percent, such as about 0.4 to about 3 percent, or in some embodiments from 0.5 to 1.5 percent by weight, based on the weight of the polymer. Examples of suitable crosslinking agents include di-olefinic compounds such as ethylene glycol dimethacrylate (EGDMA) and tetraethylene glycol dimethacrylate (TEGDMA) and other cross-linking agents such as trimethylol propane trimethacrylate (TMPTMA) which include three or more olefinic polymerizable functionalities. Generally, crosslinkers help to enhance the resulting polymer's dimensional stability.

Also, if desired an initiator can be used in the polymerization. Any initiator commonly used in the art, such as azo derivatives, like 2,2-azobis (2,4-dimethylvaleronitrile) and propanenitrile,2-methyl,2,2'-azobis or UV initiators, can be used. The initiator is used in an amount effective for initiation purposes, and is generally present from about 0.01 to 1.0 percent by weight, based on the weight of the polymer.

When a polymer is said to include a monomer such as 2-Propenoic acid, 2-methyl-,2-[4-(4,6-diphenyl-1,3,5-triazin-2-yl)-3-hydroxyphenoxy]ethyl ester, it will be understood that this means that the 2-Propenoic acid, 2-methyl-, 2-[4-(4,6-diphenyl-1,3,5-triazin-2-yl)-3-hydroxyphenoxy] ethyl ester monomer has been reacted and incorporated into the polymer.

Properties Compositions

The present polymers can be designed to have a wide range of physical characteristics. Except for UV transmittance, the present polymers will generally have substantially similar physical characteristics as the same polymer that lacks a UV absorbing compound embodied herein. By way of non-limiting example, Tables 1 and 2 show physical characteristics of a hydrophobic and a hydrophilic lens with and without the embodied triazine UV absorbers. It is understood that the present embodiments disclose a percentage of UV absorbing compound by weight of the overall dry monomers which make up the mixture suitable for polymerization, and for the purposes of this embodiments herein, when a polymer containing the UV absorbing compound is compared to the same polymer that lacks the UV absorbing compound it is understood that the missing percentage of UV absorbing may be replaced by one or more of the other co-monomeric compounds. As stated herein, substantially similar physical characteristics refers to characteristics such as for example water content, refractive index and/or glass transition temperature.

The present polymers, in some embodiments, will have 3, 4, 5, 6, 7, 8, 9, or 10 percent transmittance of UV radiation of a wavelength of 365, 366, 367, 368, 369, 370, 371, 372, 373, 374 and/or 375 nm in a formed IOL or IOL blank. In a preferred embodiment, the UV absorbing monomer will be present in an amount sufficient to impart a 10% or less transmittance of UV radiation of 370 nm in a formed IOL or IOL blank. In other preferred embodiments, the UV absorbing monomer will be present in an amount sufficient to impart a 10 9, 8, 7, 6, 5, 4, 3, 2, 1, or less percent transmittance of UV radiation of 370 nm in a formed IOL or IOL blank. The thickness of the lens will affect the UV absorbing qualities of the lens. In an embodiment the UV absorbing monomer will be present in an amount sufficient to impart a 10% or less transmittance of UV radiation of 370 nm in a formed IOL or IOL blank with a hydrated thickness of about 300 microns to about 1000 microns. In another embodiment the UV absorbing monomer will be present in an amount sufficient to impart a 10% or less transmittance of UV radiation of 370 nm in a formed IOL or IOL blank with a hydrated thickness of about 400 microns to about 900 microns. In other embodiments the UV absorbing monomer will be present in an amount sufficient to impart a 5, 6, 7, 8, 9, or 10 percent transmittance of UV radiation of 370 nm in a foldable, spherical formed IOL or IOL blank with a diopter from 0 to 35 or 10 to 30 $m^{-1}$. In another embodiment, UV absorbing monomer will be present in an amount sufficient to impart a molar extinction coefficient at 370 nm greater than 3000.

As the present polymers have been designed to be used as intraocular lenses, they also typically have a high refractive index, which is generally above about 1.40. Some of the present polymers can have a refractive index of 1.48 or higher. In an embodiment, the present polymer will have a refractive index substantially similar to the refractive index of the same polymer that lacks the UV absorbing compound embodied herein. In another embodiment, the refractive index of the present polymer will be about 0.0001% to about 0.1% higher or lower in the same polymer that lacks the UV absorbing compound. In yet another embodiment, the refractive index of the present polymer will be about 0.0001% to about 0.05% higher or lower in the same polymer that lacks the UV absorbing compound.

As the present polymers have been designed to be used as foldable intraocular lenses, when the water content is relatively low, i.e. in a hydrophobic lens, the polymerized material also typically has a relatively low glass transition temperature ($T_g$), the present polymers can be designed to have glass transition temperatures below at or about 35° C., below at or about 30° C., below at or about 25° C., such as from at or about −25° C. to at or about 35° C., 30° C., or 25° C., from about −5° C. to about 15° C., 20° C., or about 25° C. or from at or about 0° C. to at or about 15° C. A preferred range is from about −5° C. to about 15° C. In an embodiment, the present polymer will have a $T_g$ substantially similar to the $T_g$ of the same polymer that lacks the UV absorbing compound. In another embodiment, the $T_g$ of the present polymer will be 1° C. higher or lower in the same polymer that lacks the UV absorbing compound. Glass transition temperatures referred to herein may be measured at half width at a temperature change rate of 10° C./minute.

The present polymers optionally comprise hydrophobic polymers, wherein the polymer has a water content of 5.0% or less, as well as hydrophilic polymers wherein the water content is generally 20% to 30%. Other polymers with water content between that of hydrophobic and hydrophilic monomer are also contemplated. In an embodiment, the present polymer will have water content substantially similar to the water content of the same polymer that lacks the UV absorbing compound. In another embodiment, the water content of the present polymer will be 0.01% to 2.0% higher or lower in the same polymer that lacks the UV absorbing compound. In yet another embodiment, the water content of the present polymer will be 0.1% to 1.0% higher or lower in the same polymer that lacks the UV absorbing compound.

Formation of Intraocular Lens

The present embodiments herein also provide intraocular lenses made at least partially from the present polymers. Such intraocular lenses include an optic portion and one or more haptic portions. Typically, the polymers of the embodiments herein will make up part or the entire optic portion of the intraocular lens. In some embodiments, the optic portion of the lens will have a core made from one of the present polymers surrounded by different polymer or material. Lenses in which the optic portion is made up of at least partially of one of the present polymers will usually also have a haptic portion. The haptic portion can also be made of polymer of the embodiments herein or can be made of a different material, for example another polymer.

In some embodiments, the present intraocular lens is a one-piece lens having a soft, foldable central optic region and an outer peripheral region (haptic-region) in which both regions are made of the same polymer. In other embodiments, the optic and haptic regions can be formed from different types of polymers or materials, if desired. Some lenses can also have haptic portions that are made up of different materials, for example where one or more haptic portions is made from the same material as the optic portion and other haptic portions are made of materials other than a polymer of the embodiments herein. Multicomponent lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion. In an additional embodiment, the polymer may be molded into a universal blank as known in the art.

The polymers of the present embodiments herein have been designed so that they are capable of being folded so that the intraocular lens can be inserted into the eye of an individual through a small incision. The haptic portion of the lens provides the required support for the lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

Polymer Does Not Comprise Components

In one embodiment, the polymer composition does not comprise a first monomer comprising methyl methacrylate and ethylene glycol dimethacrylate. In one embodiment, the polymer composition does not comprise a first monomer consisting of methyl methacrylate and ethylene glycol dimethacrylate.

WORKING EXAMPLES

EOEMA refers to 2-ethoxyethyl methacrylate

HEMA refers to 2-hydroxyethyl methacrylate

LMA refers to lauryl methacrylate

GMA refers to glycerol methacrylate

HEA refers to 2-hydroxyethyl acrylate

TMPTMA refers to trimethylol propane trimethacrylate

DI refers to deionized water

HPTZ refers to 2-Propenoic acid, 2-methyl-,2-[4-(4,6-diphenyl-1,3,5-triazin-2-yl)-3-hydroxyphenoxy]ethyl ester

Example 1

Synthesis of HPTZ

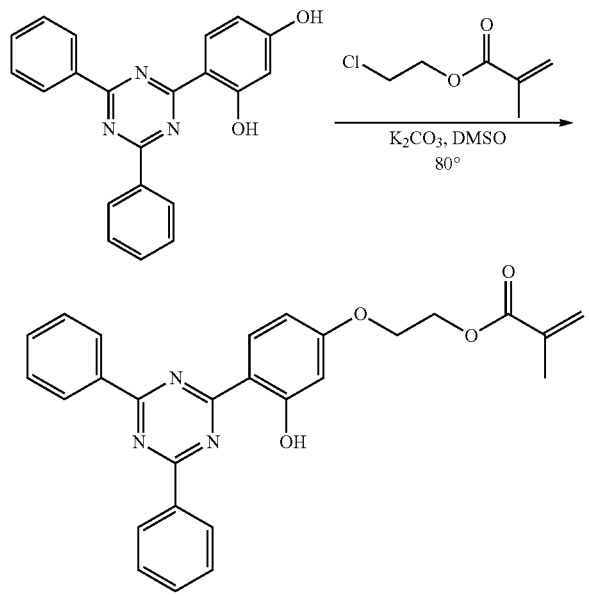

A solution of 10.8 g (31.7 mmol) of 2-(2,4-dihydroxyphenyl)-4,6-diphenyl-1,3,5-triazine, 5.8 g (39.1 mmol) of 2-chloroethyl methacrylate and 5.8 g (42.0 mmol) of anhydrous potassium carbonate in 200 ml of DMSO was heated in an oil bath preheated to 82° C. for 17.5 hours. The final bath temperature was 87° C. TLC analysis in two systems (silica gel, hexane:acetone::3:1 (v/v) and $CH_2Cl_2$) showed no starting material. After cooling to room temperature, 3×100 ml of DI water was added. A thick slurry resulted at first that became thinner with each addition of water. A noticeable exotherm was observed with each of the first two water additions, but with the third addition, the exotherm was minimal. The contents of the flask were transferred to a 1 L separatory funnel with 100 ml of DI water used to rinse the flask. The aqueous suspension was extracted with 2×200 ml of $CH_2Cl_2$ and finally with 100 ml of $CH_2Cl_2$ and the combined organic extracts were concentrated in vacuo to yield 69.1 g of wet, beige solid. The solid was treated with 3×100 ml of $CH_2Cl_2$ while refluxing. A suspension was observed until the last aliquot of $CH_2Cl_2$ was added, upon which a clear, very dark solution was obtained. After cooling to room temperature, the solution was stored in a freezer at −20° C. for 72 hours. The product began crystallizing after ~1 hour. After three days, the cold slurry was filtered and the solid washed with $CH_2Cl_2$ (prechilled to −20° C.) to yield the product as golden crystals. The crystals were dried in vacuo to constant weight to yield 8.6 g (60%) product. The material was pure by TLC ($CH_2Cl_2$) and NMR ($CDCl_3$).

Example 2

Hydrophobic Polymer 1, Suitable for use in IOL 35.0 grams of EOEMA were mixed with 2.0 grams of HEA, 2.0 grams of LMA, 1.0 grams of GMA, 0.040 grams of HPTZ, 0.021 grams of 2,2'-azobis(2,4-dimethylpentanenitrile), 0.08 grams of 2,2'-azobis(2-methylbutanenitrile) and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected.

Example 3

Hydrophobic Polymer 2, Suitable for use in IOL 35.0 grams of EOEMA were mixed with 2.0 grams of HEA, 2.0 grams of LMA, 1.0 grams of GMA, 0.050 grams of HPTZ, 0.021 grams of 2,2'-azobis(2,4-dimethylpentanenitrile), 0.08 grams of 2,2'-azobis(2-methylbutanenitrile) and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected.

Example 4

Hydrophobic Polymer 3, Suitable for use in IOL 35.0 grams of EOEMA were mixed with 2.0 grams of HEA, 2.0 grams of LMA, 1.0 grams of GMA, 0.060 grams of HPTZ, 0.021 grams of 2,2'-azobis(2,4-dimethylpentanenitrile), 0.08 grams of 2,2'-azobis(2-methylbutanenitrile) and 1.1 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected.

Example 5

Hydrophilic Polymer 1, Suitable for use in IOL 30.0 grams of HEMA were mixed with 10.0 grams of EOEMA, 0.4 grams of DI, 0.060 grams of HPTZ, 0.022 grams of 2,2'-azobis(2,4-dimethylpentanenitrile), 0.088 grams of 2,2'-azobis(2-methylbutanenitrile) and 0.6 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected.

Example 6

Hydrophilic Polymer 2, Suitable for use in IOL 30.0 grams of HEMA were mixed with 10.0 grams of EOEMA, 0.4 grams of DI, 0.050 grams of HPTZ, 0.022 grams of 2,2'-azobis(2,4-dimethylpentanenitrile), 0.088 grams of 2,2'-azobis(2-methylbutanenitrile) and 0.6 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected.

Example 7

Hydrophilic Polymer 3, Suitable for use in IOL 30.0 grams of HEMA were mixed with 10.0 grams of EOEMA, 0.4 grams of DI, 0.040 grams of HPTZ, 0.022 grams of 2,2'-azobis(2,4-dimethylpentanenitrile), 0.088 grams of 2,2'-azobis(2-methylbutanenitrile) and 0.6 grams of TMPTMA. The mixture was degassed while applying vigorous stirring. The mixture was dispensed into molds and polymerized at 70° C. for eight hours, and post-cured at 95° C. for 10 hours. The molds were allowed to cool to room temperature. The molds were opened and the polymer disc was removed and inspected.

Comparative Data for Hydrophilic Lens

Universal lens blanks were prepared according to the disclosed methods to compare refractive index and water content with lens blanks currently sold by Benz Research and Development. The universal lens blank was prepared according to the formula that is marketed under BENZ IOL 25 (UV Clear), except 0.15 wt. % of HPTZ was added to the formula. The lens blanks demonstrated the characteristics shown in Table 1. Furthermore, the loss in water content based on percent UV absorber is shown in FIG. 1.

TABLE 1

Comparative Hydrophilic Lens Data

| Lens | Water Content (%) | Refractive Index @ 20° C. (589 nm) | Refractive Index @ 35° C. (589 nm) | Refractive Index @ 20° C. (546 nm) | Refractive Index @ 35° C. (546 nm) |
|---|---|---|---|---|---|
| BENZ IOL 25 | 25.0 | 1.4603 | 1.4597 | 1.4616 | 1.4607 |
| BENZ IOL 25 with HPTZ | 25.0 | 1.4605 | 1.4595 | 1.4619 | 1.4609 |

Tolerances (589 nm)
1.460 ± 0.002 @ 20° C.
1.460 ± 0.002 @ 35° C.
Tolerances (546 nm)
1.462 ± 0.002 @ 20° C.
1.462 ± 0.002 @ 35° C.

Comparative Data for Hydrophobic Lens

Universal lens blanks were prepared according to the disclosed methods to compare refractive index with lens blanks currently sold by Benz Research and Development. The universal lens blank was prepared according to the formula that is marketed under BENZ HF1, except 0.15 wt. % of HPTZ was added to the formula. The lens blanks demonstrated the characteristics shown in Table 2.

TABLE 2

Comparative Hydrophobic Lens Data

| Lens | Refractive Index @ 20° C. (589 nm) | Refractive Index @ 35° C. (589 nm) | Refractive Index @ 20° C. (546 nm) | Refractive Index @ 35° C. (546 nm) |
|---|---|---|---|---|
| BENZ HF1 | 1.4841 | 1.4812 | 1.4869 | 1.4841 |
| BENZ HF1 with HPTZ | 1.4840 | 1.4812 | 1.4868 | 1.4842 |

Tolerances (589 nm)
1.485 ± 0.002 @ 20° C.
1.483 ± 0.002 @ 35° C.
Tolerances (546 nm)
1.487 ± 0.002 @ 20° C.
1.485 ± 0.002 @ 35° C.

Example 8

Synthesis of Second Monomer with Hydroxy-Substituted Alkyl Linker

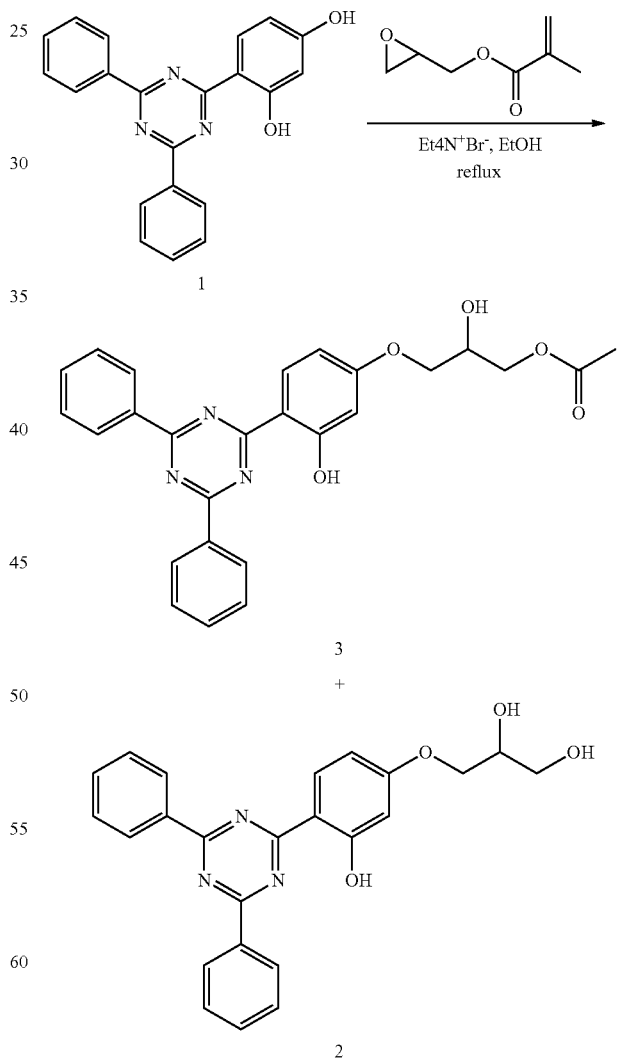

A suspension of 9.6 g (28.2 mmol) of 1, 4.8 ml (36.3 mmol) of GMA and 0.40 g of tetraethylammonium bromide (TEAB) in 100 ml of absolute EtOH was refluxed overnight (22 hours). The reaction mixture was then decanted, while still hot, into a fresh vessel, leaving a small amount of brown solid which was adhered to the flask walls behind. The decanted slurry was cooled to room temperature and placed in an ice bath for 1.5 hours. The slurry was then filtered and washed with ~100 ml of absolute EtOH (prechilled to ~−20° C.). TLC analysis (silica gel, hexane:AcCH$_3$::3:1 (v/v)) at this juncture showed the filtered solid to consist of 3 and 2 with negligible 1; the EtOH filtrate was discarded. The filtered solid was then dried in vacuo to yield 9.3 g of crude material, which was stirred in 400 ml of CH$_2$Cl$_2$ overnight.

The slurry was filtered and the recovered solid was dried to yield 3.4 g of 2 with trace 3 present (TLC); the CH$_2$Cl$_2$ filtrate comprised 3 with a small amount of impurities. A column of 275 g of silica gel (70-230 mesh) was prepared in CH$_2$Cl$_2$ and the filtrate was charged to the column, followed by elution with hexane:AcCH$_3$::3:1 (v/v). The purified product was concentrated in vacuo, the contents slurried in hexane and filtered. The product was dried in vacuo to yield 2.6 g of pure 3 as shown by NMR analysis.

What is claimed is:

1. A method of making a foldable intraocular lens capable of reducing the transmittance of ultraviolet radiation at 370 nm comprising:
   (a) polymerizing a mixture comprising:
      at least one first monomer and
      at least one second monomer comprising a trisaryl-1,3,5-triazine moiety represented by formula (I):

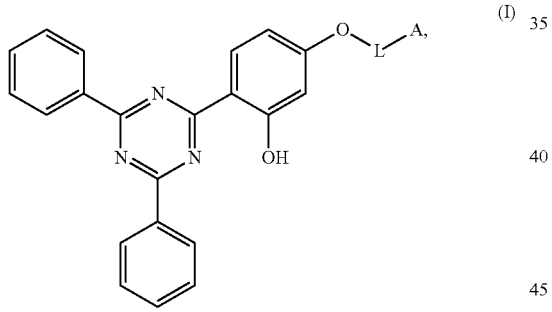

wherein L is a C$_1$ to C$_5$ alkyl, substituted by one, two, three or four hydroxyl moieties;
   A is an acrylate, methacrylate, acrylamide or methacrylamide moiety and L is covalently bound to A by the oxygen or nitrogen atom of A,
   (b) forming an optic portion from the copolymer,
      wherein the second monomer is present in about 0.05 to about 0.20 percent by weight of the overall dry mixture that is polymerized in step (a) and the transmittance of ultraviolet radiation at 370 nm in an optic portion of the lens with a hydrated thickness of about 300 microns to about 1000 microns is ten percent or less, and
      wherein the amount of the second monomer does not substantially affect a physical characteristic of the lens other than transmittance of ultraviolet radiation.

2. The method of claim 1, wherein the physical characteristic not substantially affected is refractive index.

3. The method of claim 1, wherein the physical characteristic not substantially affected is water content.

4. The method of claim 1, wherein the physical characteristic not substantially affected is glass transition temperature.

5. The method of claim 1, wherein step (a) comprises at least two different first monomers.

6. The method of claim 1, wherein the first monomers of step (a) does not comprise methyl methacrylate and ethylene glycol dimethacrylate.

7. The method of claim 1, wherein second monomer is present in about 0.15 to about 0.20 percent by weight of the overall dry mixture that is polymerized in step (a).

8. The method of claim 1, wherein the mixture of step (a) contains at least two first monomers wherein the resulting polymer has a water content of about 5 percent or less.

9. The method of claim 1, wherein the mixture of step (a) contains at least two first monomers wherein the resulting polymer has a water content of about 20 percent to about 30 percent.

10. A method of making a foldable intraocular lens capable of absorbing ultraviolet radiation at 370 nm comprising:
    (a) polymerizing a mixture comprising:
       at least one first monomer and
       at least one second monomer comprising a trisaryl-1,3,5-triazine moiety,
    (b) forming an optic portion from the copolymer
    wherein the second monomer is present in about 0.10 to about 0.20 percent by weight of the overall polymer and wherein the optic portion of the intraocular lens displays essentially the same refractive index as the optic portion of the intraocular lens formed from the polymerized mixture of (a) without the second monomer, but otherwise substantially identical conditions, wherein the second monomer is represented by formula (I):

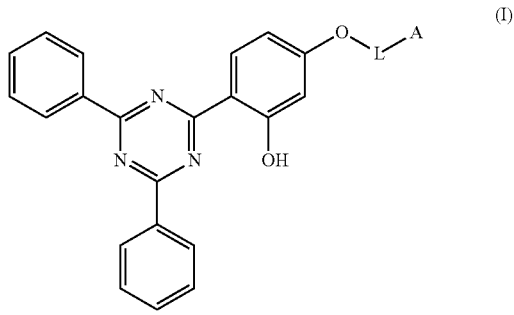

wherein L is a C$_1$ to C$_5$ alkyl, substituted by one, two, three or four hydroxyl moieties;
    A is an acrylate, methacrylate, acrylamide or methacrylamide moiety and L is covalently bound to A by the oxygen or nitrogen atom of A, and
    and the transmittance of ultraviolet radiation at 370 nm in an optic portion of the lens with a hydrated thickness of about 300 microns to about 1000 microns is ten percent or less.

11. The method of claim 10, wherein step (a) comprises at least two first monomers.

12. The method of claim 10, wherein the first monomers of step (a) comprises an acrylate or methacrylate moiety and at least one additional moiety covalently bonded to the O of the acrylate or methacrylate moiety.

13. The method of claim 10, wherein the optic portion of the intraocular lens displays essentially the same water content as the optic portion of the intraocular lens formed from the polymerized mixture of (a) without the second monomer, but otherwise identical conditions.

14. The method of claim 10, wherein the intraocular lens has a transmittance of three percent or less of ultraviolet radiation at a wavelength of about 370 nm.

15. The method of claim 10, wherein the intraocular lens has a transmittance of six percent or less of ultraviolet radiation at a wavelength of about 370 nm.

16. The method of claim 10, wherein second monomer is present in about 0.13 to about 0.17 percent by weight of the overall polymer.

17. The method of claim 10, wherein the first compound does not comprise methyl methacrylate and ethylene glycol dimethacrylate.

18. The method of claim 10, wherein (b) comprises cutting, milling or both cutting and milling the intraocular lens blank into the optic portion.

19. A method for modifying an individual's eyesight, comprising inserting the intraocular lens prepared by method comprising claim 1 into an eye of a subject.

20. The method of claim 19, further comprising folding the intraocular lens prior to inserting the intraocular lens into the eye and allowing the intraocular lens to unfold after it is inserted into the eye.

21. A method for increasing the extinction coefficient of a copolymer of ultraviolet radiation at 370 nm through a foldable intraocular lens comprising:
(a) incorporating a monomer comprising a 4-(4,6-diphenyl-1,3,5-triazin-2-yl)-3-hydroxyphenoxy moiety into at least one polymer and
(b) forming the polymer into a material suitable for use as an intraocular lens, wherein the monomer comprising a 4-(4,6-diphenyl-1,3,5-triazin-2-yl)-3-hydroxyphenoxy moiety comprises 0.10 to 0.15 weight percent of the overall dry polymer, wherein the monomer comprising a 4-(4,6-diphenyl-1,3,5-triazin-2-yl)-3-hydroxyphenoxy moiety is represented by formula (I):

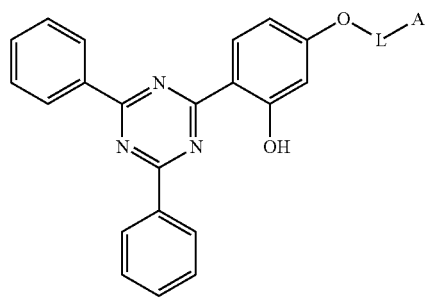

wherein L is a $C_1$ to $C_5$ alkyl, substituted by one, two, three or four hydroxyl moieties;
A is an acrylate, methacrylate, acrylamide or methacrylamide moiety and L is covalently bound to A by the oxygen or nitrogen atom of A, and
and the transmittance of ultraviolet radiation at 370 nm in an optic portion of the lens with a hydrated thickness of about 300 microns to about 1000 microns is ten percent or less.

22. A method for preventing the transmittance of at least 90% of ultraviolet radiation at 370 nm through a foldable intraocular lens comprising:
(a) incorporating a monomer comprising a 4-(4,6-diphenyl-1,3,5-triazin-2-yl)-3-hydroxyphenoxy moiety into at least one polymer and
(b) forming the polymer into a material suitable for use as an intraocular lens, wherein the monomer comprising a 4-(4,6-diphenyl-1,3,5-triazin-2-yl)-3-hydroxyphenoxy moiety comprises 0.10 to 0.15 weight percent of the overall dry polymer, wherein the monomer comprising a 4-(4,6-diphenyl-1,3,5-triazin-2-yl)-3-hydroxyphenoxy moiety is represented by formula (I):

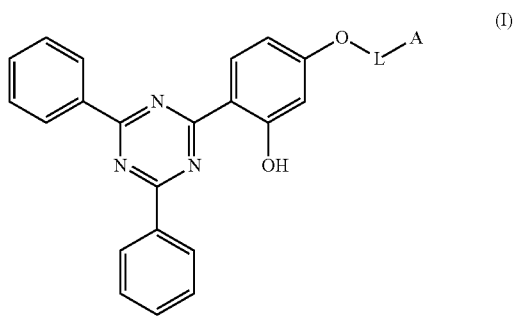

wherein L is a $C_1$ to $C_5$ alkyl, substituted by one, two, three or four hydroxyl moieties;
A is an acrylate, methacrylate, acrylamide or methacrylamide moiety and L is covalently bound to A by the oxygen or nitrogen atom of A, and
and the transmittance of ultraviolet radiation at 370 nm in an optic portion with a hydrated thickness of about 300 microns to about 1000 microns is ten percent or less.

23. The method of claim 22, wherein the foldable intraocular lens has a transmittance of nine percent or less of ultraviolet radiation at a wavelength of about 370 nm.

24. The method of claim 22, wherein the foldable intraocular lens has a transmittance of six percent or less of ultraviolet radiation at a wavelength of about 370 nm.

25. The method of claim 22, wherein the polymer does not comprise methyl methacrylate or ethylene glycol dimethacrylate.

26. The method of claim 22, wherein the polymer has essentially the same refractive index as a polymer without the monomer comprising a 4-(4,6-diphenyl-1,3,5-triazin-2yl)-3-hydroxyphenoxy moiety, but otherwise identical composition.

27. The method of claim 22, wherein the polymer has essentially the same water content as a polymer without the monomer comprising a 4-(4,6-diphenyl-1,3,5-triazin-2-yl)-3-hydroxyphenoxy moiety, but otherwise identical composition.

28. A foldable intraocular lens or lens blank comprising at least one copolymer comprising at least (a) one first monomer, and
(b) a second monomer present in about 0.05 to about 0.20 percent by weight of the overall dry polymer comprising a 4-(4,6-diphenyl-1,3,5-triazin-2-yl)-3-hydroxyphenoxy moiety, and wherein the optic portion of the intraocular lens displays essentially the same refractive index as the optic portion of a intraocular lens formed from the polymerized mixture of (a) without the second monomer, but otherwise identical composition, wherein the monomer comprising a 4-(4,6-diphenyl-1,3,5-triazin-2-yl)-3-hydroxyphenoxy moiety is represented by formula (I):

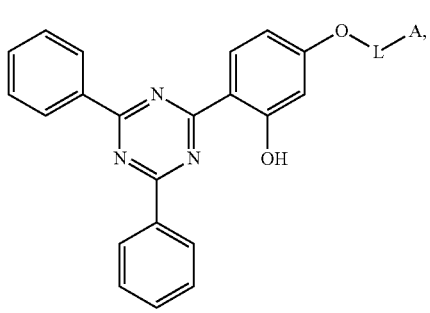

wherein L is a $C_1$ to $C_5$ alkyl, substituted by one, two, three or four hydroxyl moieties;

A is an acrylate, methacrylate, acrylamide or methacrylamide moiety and L is covalently bound to A by the oxygen or nitrogen atom of A, and and the transmittance of ultraviolet radiation at 370 nm in an optic portion in the lens or formed from the lens blank with a hydrated thickness of about 300 microns to about 1000 microns is ten percent or less.

29. The lens of claim 28, wherein the second monomer is present in about 0.13 to about 0.17 percent by weight of the overall dry polymer.

30. The lens of claim 28, wherein the second monomer has an extinction coefficient of at least 3000 $M^{-1}cm^{-1}$ for radiation at 370 nm.

31. The lens of claim 28, wherein the lens has a transmittance of nine percent or less of ultraviolet radiation at a wavelength of about 370 nm.

32. The lens of claim 28, wherein the lens has a transmittance of six percent or less of ultraviolet radiation at a wavelength of about 370 nm.

33. The method of claim 1, wherein L is a $C_1$ to $C_5$ alkyl substituted by one or two hydroxyl moieties and A is an acrylate or methacrylate.

34. The method of claim 1, wherein L is a $C_1$ to $C_5$ alkyl substituted by one hydroxyl moiety and A is an acrylate or methacrylate.

35. The method of claim 1, wherein L is a $C_3$ alkyl substituted by one hydroxyl moiety and A is an acrylate or methacrylate.

36. The method of claim 1, wherein L is represented by the formula —$CH_2CH(OH)CH_2$— and A is an acrylate or methacrylate.

37. The method of claim 10, wherein the second monomer is represented by formula (III):

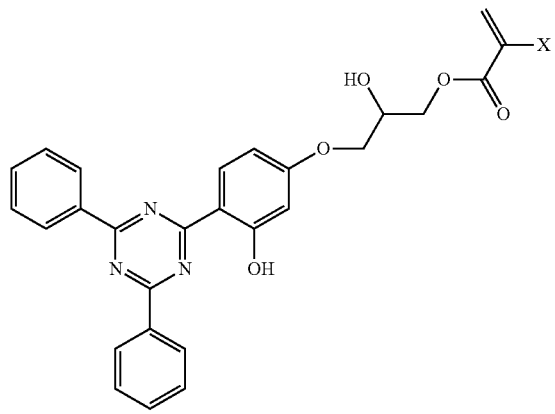

wherein X is H or $CH_3$.

38. The method of claim 22, wherein L is a $C_1$ to $C_5$ alkyl substituted by one or two hydroxyl moieties and A is an acrylate or methacrylate.

39. The method of claim 22, wherein L is a $C_1$ to $C_5$ alkyl substituted by one hydroxyl moiety and A is an acrylate or methacrylate.

40. The method of claim 22, wherein L is represented by the formula —$CH_2CH(OH)CH_2$— and A is an acrylate or methacrylate.

41. The method of claim 22, wherein the second monomer is represented by formula (III):

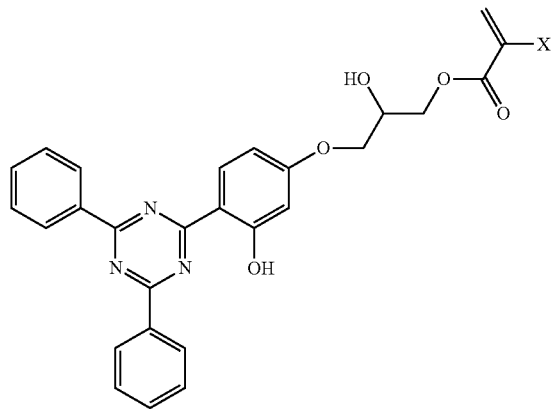

wherein X is H or $CH_3$.

42. The lens of claim 28, wherein L is a $C_1$ to $C_5$ alkyl substituted by one or two hydroxyl moieties and A is an acrylate or methacrylate.

43. The lens of claim 28, wherein L is a $C_1$ to $C_5$ alkyl substituted by one hydroxyl moiety and A is an acrylate or methacrylate.

44. The lens of claim 28, wherein L is represented by the formula —$CH_2CH(OH)CH_2$— and A is an acrylate or methacrylate.

45. The lens of claim 28, wherein the second monomer is represented by formula (III):

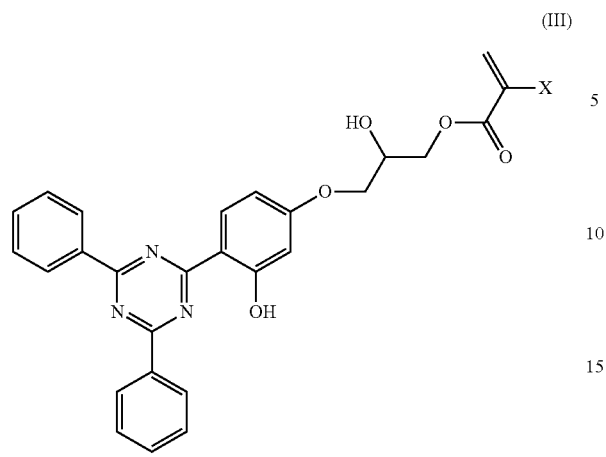
(III)
wherein X is H or CH$_3$.
* * * * *